United States Patent [19]
McGuinness et al.

[11] Patent Number: 5,948,407
[45] Date of Patent: Sep. 7, 1999

[54] ORAL INDUCTION OF TOLERANCE TO PARENTERALLY ADMINISTERED NON-AUTOLOGOUS POLYPEPTIDES

[75] Inventors: Charlotte M. McGuinness, Rockville; Beth A. Burnside, Silver Spring; Edward M. Rudnik, North Potomac, all of Md.

[73] Assignee: Shire Laboratories Inc., Rockville, Md.

[21] Appl. No.: 09/045,886

[22] Filed: Mar. 18, 1998

Related U.S. Application Data

[60] Provisional application No. 60/039,633, Mar. 19, 1997.
[51] Int. Cl.$^6$ .......................... A01N 63/00; A61K 38/37; A61K 35/02; A61K 38/28
[52] U.S. Cl. .................. 424/184.1; 424/93.1; 424/520; 424/810; 514/2; 514/3; 514/8; 514/21; 530/303; 530/350; 530/383; 530/384
[58] Field of Search .................. 424/439, 464, 424/184.1, 810, 93.1, 520; 530/383, 384, 303, 350; 514/2, 3, 8, 21

[56] References Cited

U.S. PATENT DOCUMENTS

| | | |
|---|---|---|
| 5,720,955 | 2/1998 | Weiner et al. . |
| 5,733,547 | 3/1998 | Weiner et al. . |
| 5,763,396 | 6/1998 | Weiner et al. . |
| 5,783,188 | 7/1998 | Weiner et al. . |

OTHER PUBLICATIONS

Miller, A., et al. (1993) "Suppression of experimental autoimmune encephalomyelitis by oral administration of myelin basic protein: V.I. Suppression of adoptively transferred disease and differential effects of oral vs. intravenous tolerization," *Journal of Neuroimmunology*, 46: 73–82.

Trentham, D.E., et al. (1993) "Effects of Oral Administration of Type II Collagen on Rheumatoid Arthritis," *Science*, 261: 1727–1729.

Kaufman, D.L., et al. (1993) "Spontaneous loss of T–cell tolerance to glutamic acid decarboxylase in murine insulin–dependent diabetes," *Nature*, 366: 69–70.

Weiner, H.L., et al. (1994) "Oral Tolerance: Immunologic Mechanisms and Treatment of Animal and Human Organ–Specific Autoimmune Diseases by Oral Administration of Autoantigens," *Annu. Rev. Immunol.*, 12: 809–837.

Al–Sabbagh, A., et al. (1994) "Antigen–driven tissue–specific suppression following oral tolerance: orally administered myelin basic protein suppresses proteolipid protein–induced experimental autoimmune encephalomyelitis in the SJL mouse," *Eur. J. Immunol.*, 24: 2104–2109.

Khare, S.D., et al. (1995) "Oral Administration of an Immunodominant Human Collagen Peptide Modulates Collagen–Induced Arthritis," *The Journal of Immunology*, 155: 3653–3659.

Ruedl, C., et al. (1996) "Humoral and cellular immune responses in the murine respiratory tract following oral immunization with cholera toxin or *Escherichia coli* heat–labile enterotoxin," *Vaccine*, 14(8): 792–798.

Chen, Y., et al. (1996) "Oral tolerance in myelin basic protein T–cell receptor transgenic mice: Suppression of autoimmune encephalomyelitis and dose–dependent induction of regulatory cells," *Proc. Natl. Acad. Sci. USA*, 93: 388–391.

Vandenbark, A.A., et al. (1996) "Treatment of multiple sclerosis with T–cell receptor peptides: Results of a double–blind pilot trial," *Nature Medicine*, 2(10): 1109–1115.

Blanas, E., et al. (1996) "Induction of Autoimmune Diabetes by Oral Administration of Autoantigen," *Science*, 274: 1707–1709.

Hoyer, Leon W., "Future Approaches to Factor VIII Inhibitor Therapy," *The American Journal of Medicine*, 91(5A):40S–44S (1991).

Nilsson, et al., "Noncoagulation Inhibitory Factor VIII Antibodies After Induction of Tolerance to Factor VIII in Hemophilia A Patients," *Blood*, 75(2):378–383 (1990).

Sun, et al., "Cholera toxin B Subunit: An efficient transmucosal carrier–delivery system for induction of peripheral immunological tolerance," *Proc. Natl. Acad. Sci.*, 91:10795–10799 (1994).

Weiner, Howard L., "Oral Tolerance," *Proc. Natl. Acad. Sci.*, 91:10762–10765 (1994).

*Primary Examiner*—David Saunders
*Assistant Examiner*—F. Pierre VanderVegt
*Attorney, Agent, or Firm*—Elliot M. Olstein; Raina Semionow

[57] ABSTRACT

Disclosed is a method for reducing an immune response to a parenterally administered non-autologous antigen in an individual who is immunologically responsive thereto by mucosally administering to the individual an amount of the antigen effective to reduce any immune response to parenteral administration of said antigen. The antigen can be a polypeptide such as a hormone, like insulin, which supplements a metabolic deficiency in the recipient of a polypeptide intended to serve the same function. The polypeptide can also be one which supplements a deficiency in the production of a physiologically important polypeptide, such as a hematologic regulatory factor. The hematologic regulatory factor can enhance or inhibit thrombogenesis or platelet deposition. Also, the antigen can be a tissue or cell preparation, such as of allogeneic or xenogeneic tissue or cells. The method for reducing an immune response is preferably one which induces tolerance to parenteral administration of the antigen, such as by inducing or elevating a suppressor T cell response to the mucosally administered antigen.

16 Claims, No Drawings

ORAL INDUCTION OF TOLERANCE TO PARENTERALLY ADMINISTERED NON-AUTOLOGOUS POLYPEPTIDES

This application is a utility application based on provisional application Ser. No. 60/039,633 filed Mar. 19, 1997.

A significant cause of morbidity and mortality in this country is disease that results from patients' inability to produce enough of certain bioactive proteins. The only treatment for many of these diseases is replacement therapy. That is, human, animal, plant or recombinant proteins are administered to these patients to cure their deficiencies. In a subpopulation of patients, the immune system recognizes the injected protein as foreign and mounts an immune response. This can take many forms. Some patients make neutralizing antibodies that destroy the protein, while others have immune reactions that can include platelet aggregation and anaphylactic shock. Affected patients must then either switch to an alternate form of the protein, for example porcine rather than human insulin, or increase their dosage to overcome the neutralizing antibodies, for example increased doses of Factor VIII [1]. Thus, these patients are often hard to treat and may be denied effective therapies.

Many human proteins used for replacement therapy are expensive and scarce, since they are large, complex, and often glycosylated, which makes them difficult to produce, even using recombinant techniques. Non-human proteins, such as porcine or bovine, are often poorly tolerated. The availability of heterologous proteins to be used for replacement therapy has resulted in the risk of immune reactions to such proteins.

Food proteins that have been ingested normally, may pass through the intestinal wall in a relatively intact form and a small percentage pass into the blood. Only rarely, however, do adults mount an immune reaction to these food proteins, resulting in food allergy. Normally immune reactions to dietary proteins are suppressed by the mechanism of oral immune-tolerance [2]. Some proteins and protein fragments, in the course of digestion, are taken up by specialized intestinal cells, either enterocytes or Peyer's Patch cells. These are antigen presenting cells. They present the peptides to the gut associated lymphoidal system which generates suppressor T-cells that recognize the peptide. Antigen specific T-cells are found in lymphoidal tissue within twenty four hours of antigen feeding. These cells suppress immune reactions via release of transforming growth factor beta (TGF-β). TGF-β down-regulates immune responsive cells. Suppressor T-cells suppress immune reactions to the dietary peptides they recognize for up to one month [3].

Immune-tolerance to enterically absorbed proteins can be induced by presentation of a portion of the protein to the immune cells by antigen presenting cells in the lung or intestine. Lung epithelial cells, like intestinal epithelial cells, are antigen presenting cells. They present antigens to pulmonary associated lymphoidal tissue. Uptake by antigen presenting cells can be achieved therapeutically by oral, enteral, or inhalation administration of the protein or a portion of the protein. This mechanism has been used to tolerize patients with autoimmune diseases by suppressing the reaction against tissue specific antigens. For example, therapies are now being developed to tolerize individuals to organ-specific diseases, such as tolerization of multiple sclerosis patients to myelin basic protein and rheumatoid arthritis patients to collagen.

SUMMARY OF THE INVENTION

The purpose of this invention is to suppress or reduce the immune response many patients mount to parenterally administered therapeutic polypeptides, such as Factors V, VIII and IX, human plasma proteins, as well as reactions to other injected proteins and peptides or protein drugs. This includes portions of these proteins, recombinant forms, protease cleaved proteins or portions or fragments of proteins, synthesized fragments and analogs, and animal homologs.

The present invention is based on the discovery that oral, enteral or inhalation administration of heterologous proteins, or their biologically active peptide fragments, in small amounts, is a particularly effective means of suppressing T-cell-mediated, T-cell dependent immune reactions, or other immune reactions, which inhibit replacement therapy for disorders such as diabetes or hemophilia in humans. Thus, as demonstrated below, the simple method of administration, orally, enterally or by inhalation, of at least one therapeutically active protein, polypeptide, or active fragments or analogs of at least one of them, as taught by the invention, is an effective treatment to suppress the development of an inhibitory response. Furthermore, the compositions and method of the invention do not have the drawbacks associated with prior art therapeutic or palliative agents and techniques.

Accordingly, the invention provides a method for reducing an immune response to a parenterally administered non-autologous antigen in an individual who is immunologically responsive thereto by mucosally administering to the individual an amount of the antigen effective to reduce any immune response to parenteral administration of said antigen. The antigen can be a polypeptide (including heterologous proteins and glycoproteins). One such polypeptide type can be a hormone, like insulin, which supplements a metabolic deficiency in the recipient of a polypeptide intended to serve the same function. The polypeptide can also be one which supplements a deficiency in the production of a physiologically important polypeptide, such as a hematologic regulatory factor. The hematologic regulatory factor can enhance or inhibit thrombogenesis or platelet deposition. Also, the antigen can be a tissue or cell preparation, such as of allogeneic or xenogeneic tissue or cells. The method for reducing an immune response is preferably one which induces tolerance to parenteral administration of the antigen, such as by inducing or elevating a suppressor T cell response to the mucosally administered antigen.

DETAILED DESCRIPTION OF PREFERRED EMBODIMENTS

"Active fragment" of protein describes any synthetic peptide or polypeptide construct containing one or more partial amino acid sequences of the protein and possessing the ability to suppress or eliminate inhibitory immune response thereto, upon oral, enteral respiratory administration. This definition thus excludes fragments of these plasma protein that do not produce suppression of the immune response in vitro, e.g. in a lymphocyte proliferation assay or in vivo, e.g. in a rodent model or in a human.

"Active analogs" of protein include compounds that are structurally related to the protein or to active fragments thereof. As such, the term includes, without limitation, any combination of their polypeptide domains or fragments possessing the ability to eliminate or suppress immune responses to the protein, upon oral, enteral or by-inhalation administration. The term "analog" also encompasses any polypeptide which differs from the amino acid sequence of the parent protein by one or more amino acids while still retaining substantially equivalent ability to suppress inhibitory immune response to replacement therapy. "Oral" administration includes oral, enteral or intragastric administration. Oral administration which does not bypass the stomach may be preferred.

Oral, enteral or inhalation-induced tolerance is dose-dependent over a broad range of oral, enteral and inhalant dosages. However, there may be minimum and maximum effective dosages. As is understood by one skilled in the art, this means that suppression of both clinical and biochemical symptoms of inhibitors to replacement therapy in a particular disease occurs within a specific dosage range which varies with the structure and function of the protein administered, whether it is whole protein or discrete peptide fragment(s) or analog(s), as well as the solubility and purity of the peptides or polypeptides. Consequently, adjustment and refinement of the dosages used and administration schedules must be determined based on these factors, and may need to be determined experimentally. Such determinations, however, require no more than routine experimentation.

Generally, the preferred way to accomplish suppression of the immune responses against the injected protein is the administration, orally, enterally or by inhalation of purified or highly purified water-soluble whole protein or biologically active peptide fragment(s) thereof in an amount from about 0.05 to about 10 mg/day. The administration of proteins or their biologically active peptide fragments or analogs may be accomplished in a single dose form or multiple dose form. Preferably, the whole protein is administered at dosages from 0.1 to 10 milligram per day. The foregoing dosages are easily extrapolated to a range of whole proteins as well as to fragments and analogs.

If specific, active fragments are used to induce tolerance, it may be necessary to protect them from digestion and breakdown in the stomach. The invention also includes delivery of active fragments in a relatively intact form to the antigen presenting cells of the intestine. This can be accomplished by incorporating peptides into a microemulsion or a beadlet dosage. Such forms are well known in the art to include enteric coating as necessary. Protection of active fragments allows lower dosages to be used to achieve therapeutic levels.

The present invention provides oral pharmaceutical formulations for treating patients suffering from a variety of disorders with inhibitors, comprising an amount of whole protein or biologically active peptide fragment(s) or analogs that effectively suppress immune inhibitors. Liquid aqueous formulations containing soluble protein liquid and solid compositions can also be administered.

Throughout this disclosure, it is disclosed that any clinically or statistically significant attenuation of even one symptom of the disorder under treatment is within the scope of the invention.

Each oral, enteral or inhalable formulation according to the present invention may additionally comprise inert constituents including pharmaceutically acceptable carriers, diluents, fillers, solubilizing or emulsifying agents, and salts, as is well-known in the art. For example, tablets may be formulated in accordance with conventional procedures employing solid carriers well-known in the art. Hard and soft capsules employed in the present invention can be made from any pharmaceutically acceptable material, such as gelatin. Capsules, especially important in this invention are soft gelatin capsules, or cellulosic derivatives. Sustained release oral delivery systems and/or enteric coatings for orally administered dosage forms are also contemplated [6].

In another aspect of the invention, one can use emulsions to orally deliver the active agent, which protects the peptides until they reach the antigen presenting cells in the intestine. This embodiment is particularly useful for delivery of active peptide fragments that require protection from degradation in the intestine. An emulsion is a dispersed system containing at least two immiscible liquid phases, a hydrophobic phase and a hydrophilic phase. The emulsion comprises the dispersed phase, the dispersion phase and an emulsifying agent or surfactant agent, except when the hydrophobic material is a "self-emulsifying" ester, whereby it is possible to produce an emulsion without a separate emulsifying agent. Usually one of the two immiscible liquids is an oil while the other is aqueous. Which phase becomes the dispersed phase depends on the relative amounts of the two liquid phases and which emulsifying agent is selected. Therefore, an emulsion in which the aqueous phase in the discontinuous phase is called a water-in-oil (w/o) emulsion and vice versa. The term "colloidal" refers to emulsions in which the dispersed phase is of very fine particles, usually less than about 1 mm in size. A "microcolloid" is an emulsion wherein the dispersed particles are usually about 300 µm or less in size. Cosurfactants are also common components of microcolloids and are simply surfactants included in addition to the primary surfactant.

A "microemulsion" is an optically clear, isotropic and thermodynamically stable liquid. Microemulsions are composed of an oily phase, an aqueous phase, a surfactant, and sometimes, a cosurfactant. A homogenous mixture forms when components of the microemulsion are mixed together in any order. The resulting composition is thermodynamically stable with either a water continuous phase, an oily continuous phase, or a bicontinuous combination of the phases. Specifically, the microemulsion of the invention is a water-in-oil microemulsion, with the oil as the continuous phase.

Microemulsions are ideal for oral peptide fragment systems since they are homogenous, thermodynamically stable, have uniform droplet sizes of approximately 200–400 µm and are optically clear. A water-in-oil microemulsion, in particular, has small aqueous phase droplets, uniformly dispersed in a continuous oil phase. Therefore, the peptide is protected from proteolytic enzymes that are soluble in the digestive fluids. In general, the chemical structure of a peptide dictates that it will be at least somewhat, if not mostly, water soluble, and thus will be located inside the water droplet or very near the surface of the droplet of the water-in-oil microemulsion system. Thus, the outer oily phase of the microemulsion prohibits migration of proteolytic enzymes through the delivery system. The outer oily phase of the microemulsion is also able to incorporate into the intestinal cell matrix, thus creating membrane channels through which the peptide can pass. One general preparation procedure that maximizes peptide solubility is as follows: first, the peptide is prepared as a slurry in the aqueous phase at pH 2; second, the surfactant is added and mixed thoroughly; third, the oily phase is added and mixed to form the microemulsion.

The ingredients of the microemulsion can include any of the below named surfactants, oily phases or aqueous phases. The emulsions can either be macro- or microemulsions. Ordinary materials that are used to make emulsified hydrophobic and hydrophilic phases are contemplated. These materials include, but are not limited to, surfactants, aqueous and nonaqueous hydrophilic materials and numerous hydrophobic materials. Non-limiting examples of surfactants are polyoxyethylene sorbitan esters, ethyleneoxide propylene oxide block copolymers, polyglycolized glycerides, sucrose esters, polyoxyethylene laurel esters, and others. Non-limiting examples of hydrophilic materials are various aqueous buffered systems, polyethylene glycols, diethylene glycol monoethyl ether, and others. Non-limiting examples of hydrophobic materials are carboxylic acid esters, fatty acids, glyceryl derivatives such as glyceryl behenate, short, medium and long chain triglycerides and others.

Macro or gross emulsions can be made by conventional emulsion methods. In largescale manufacture, these steps can be accomplished using standard mixing equipment employed in the production of ointments, creams and lotions. Specifically, mixing tanks made by Lee Industries (New Cumberland, Pa.) can be readily used. Regardless of the equipment employed, mixing needs to be accomplished using as low a shear rate as practical, in order to maintain the physical integrity of the peptide. The bioactive agent can be added to the cooled mixture at a suitable temperature for stability and activity purposes. Microemulsions, which are spontaneously formed, isotopically clear liquids are formed with mechanical mixing of the ingredients. The bioactive agent can be added either to the hydrophilic phase prior to mixing with the surfactant and hydrophobic phases or after the microemulsion is formed, depending on stability and activity of the bioactive agent. The emulsions can be filled into hard or soft gelatin capsules and optionally coated with enteric polymers.

The incorporated peptide/protein is further protected from peptidases and proteases with the addition of a hydrophobic thickening agent in the oily phase. An additional hydrophobic ingredient, when added to the microemulsion, forms a paste-like composition that becomes liquefied at about 37° C.

The active fragments or analogs can be incorporated into a hydrophobic beadlet or particle as disclosed by Rudnic et al. (U.S. Pat. No. 5,430,021) [7]. The hydrophobic particles are compresses of long chain carboxylic acids or esters. The particles can be incorporated into a tablet that can then be enterically coated, so that it is protected in the stomach and released in the intestine. And, likewise, the beadlets can be enterically coated and then filled into a hard gelatin capsule for the same purpose.

Alternately, the bioactive material can be coated or loaded on to spheres which are commercially available or formed into beadlets made by current fluid bed spray congealing, spray-drying or hot-melt technologies, in addition to the appropriate absorption enhancer for the specific bioactive agent. These can be optionally coated then filled into hard gelatin capsules or compressed into a tablet dosage form.

In an alternative embodiment, whole proteins or separated large protein domains or chains are formulated. Because these large proteins can benefit from partial breakdown in the stomach and intestine before reaching antigen presenting cells, these can be incorporated into dosage forms that do not provide extensive protection from proteases. Examples of such dosage forms are incorporated into tablets or capsules with solid carriers. Examples of solid carriers include starch, cellulose, sugar, bentonite, silica, and other commonly used carriers. Further examples of carriers and diluents which may be used in the formulations of the present invention include lactose microcrystalline cellulose, modified cellulosics for rapid disintegration, dextrose and water.

In yet another embodiment of the present invention, the pharmaceutical formulations or dosage forms are administered to humans suffering from diseases such as hemophilia, by inhalation, preferably in aerosol form. The inhalation mode of administration is preferably not through the nasal mucosa but through the bronchial and pulmonary mucosa. Lower amounts of whole protein, eg. Factor VIII or Factor IX or their active fragment(s) or analog(s) in the case of hemophilia, are required using aerosol administration. The amounts of whole protein or its active peptide fragment(s) or analog(s) which are administered in an aerosol dosage form are generally between about 0.01 milligram and about 5 milligrams per day (and preferably 0.01 to 0.5 mg per day) and can be administered in single or multiple dosage forms. The exact amount to be administered may vary depending on the state and severity of a patient's disease and the physical condition of the patent and is a matter of routine optimization.

The aerosol pharmaceutical formulations of the present invention may include, as optional ingredients, pharmaceutically acceptable carriers, diluents, solubilizing and emulsifying agents, and salts that are well-known in the art. Examples of such substances include normal saline solutions, such as physiologically buffered saline solutions, and water.

The route of administration of therapeutic protein or their active fragment(s) or analog(s) according to this embodiment of the present invention is in an aerosol or inhaled form. The whole protein or its active fragment(s) can be administered as dry powder particles or preferably as an atomized aqueous solution suspended in a carrier gas (i.e. air or nitrogen). Preferred aerosol pharmaceutical formulations can include, for example, a physiologically-acceptable buffered saline solution containing between about 0.01 milligram and up to about 5 (preferably up to about 0.5) milligrams of the therapeutic protein or its active fragment(s) or analog(s). Dry aerosol in the form of finely divided solid particles of whole protein or its biologically active peptide fragment(s) that are not dissolved or suspended in a liquid are also useful in the practice of the present invention. The whole protein or its active fragment(s) or analog(s) can be in the form of dusting powders and comprise finely divided particles having an average particle size of between 1 and 5 microns, preferably between 2 and 3 microns. Finely divided particles can be prepared by pulverization and screen filtration using techniques well known in the art. The particles may be administered by inhaling a predetermined quantity of the finely divided material, which can be in the form of a powder.

Other systems of aerosol delivery, such as the pressurized metered dose inhaler (MDI) and the dry powder inhaler as disclosed in Newman, S. P. in Aerosols and the Lung, Clarke, S. W. and Davia, D., eds., pp. 197–224, Butterworths, London, England, 1984, can be used when practicing the present invention.

Aerosol delivery systems of the type described herein are available from numerous commercial sources including Fisons Corporation (Bedford, Mass.), Schering Corp. (Kenilworth, N.J.) and American Pharmoseal Co. (Valencia, Calif.).

It will be appreciated that unit content of active ingredient(s), whole plasma proteins or their active fragment(s) or analog(s), contained in an individual dose of each dosage form need not in itself constitute an effective amount, since the necessary effective amount can be reached by administration of a plurality of dosage units (such as capsules or tablets or combinations thereof). Administration of an effective dosage may be in a single dose form or in multiple dosage forms and it may be provided with an enteric coating and/or a sustained release mechanism, such as a degradable matrix or a reservoir.

Where whole protein or its biologically active peptide fragment(s) are introduced orally or enterally, they can be mixed with other ingestible forms and consumed in solid, semi-solid solution, suspension, or emulsion form. It may also be mixed in conjunction or alternatively with pharmaceutically acceptable carriers, flavor enhancers, water, suspending agents and emulsifying agents.

The following examples illustrate but do not limit the invention.

Microemulsions in Soft Gelatin Capsules for Oral Administration of Bioactive Agents

EXAMPLE 1

|  | % |
| --- | --- |
| Pluronic L44 | 26.7 |
| Linoleic Acid | 62.5 |
| Aqueous | 9.8 |
| Bioactive Agent | 1.0 |

Mix ingredients together and fill into soft gelatin capsules.

EXAMPLE 2

|  | % |
| --- | --- |
| Pluronic L44 | 26.0 |
| Linoleic Acid | 60.6 |
| Aqueous | 9.4 |
| Bioactive Agent | 4.0 |

Mix ingredients together and fill into soft gelatin capsules.

EXAMPLE 3

|  | % |
| --- | --- |
| Glyceryl monostearate | 99 |
| Bioactive Agent | 1.0 |

Heat ingredients in suitable stirred, jacketed container. Spray into fluid bed or spray congealing tower to form beadlets.

EXAMPLE 4

|  | % |
| --- | --- |
| Glyceryl monostearate | 97 |
| Citric Acid or other pH modifier/stabilizer | 1.0 |
| Bioactive Agent | 1.0 |
| SLS | 1.0 |

Heat ingredients in suitable stirred, jacketed container. Spray into fluid bed or spray congealing tower to form Beadlets.

Oral Administration of Bioactive Agent—with Enteric Coating for Targeted Delivery to the Small Intestine.

EXAMPLE 5

|  | % |
| --- | --- |
| glyceryl behenate (Compritol 888 ATO) | 45 |
| Labrasol | 4.5 |
| Bioactive Agent | 1.0 |
| Eudragit L30D-55 | 47.5 |
| talc | 1.0 |
| Colloidal Silicon Dioxide (Cab-O-Sil) | 1.0 |

Place Compritol in fluid bed. Mix surfactant and active agent and spray into Compritol. Heat to form beadlets. Coat with polymer and dust with talc and Cab-O-Sil.

Oral Administration of Bioactive Agent—Intended for Entire Intestinal Coverage.

EXAMPLE 6

|  | % |
| --- | --- |
| glyceryl monostearate | 20 |
| stearic acid | q.s. to 30 |
| Bioactive Agent | 5.0 |
| Eudragit L30D-55 | 24 |
| Eudragit 411OD | 25 |

Form beadlets by methods described in Examples 3 to 5 and coat with either one of the polymers listed for enteric and colonic delivery.

Lung Delivery—Nebulizer Formula

EXAMPLE 7

|  | % |
| --- | --- |
| Bioactive Agent | 1.0 |
| Water | 92.88 |
| Microcrystalline Cellulose | 1.0 |
| Sodium Carboxymethyl Cellulose | 0.1 |
| benzalkonium chloride | 0.01 |
| polysorbate 80 | 0.01 |
| phenyl ethyl alcohol | 5.0 |
| pH to 6.4 (5.5 to 6.8) |  |

Mix together ingredients. Mix well to form suitable solution. Adjust pH with appropriate buffer. Fill into nebulizer apparatus.

EXAMPLE 8

|  | % |
| --- | --- |
| Bioactive Agent | 1.0 |
| Water | 77.88 |
| Microcrystalline Cellulose | 1.0 |
| Sodium Carboxymethyl Cellulose | 0.1 |
| benzalkonium chloride | 0.01 |
| polysorbate 80 | 0.01 |

-continued

| | % |
|---|---|
| phenyl ethyl alcohol | 20 |
| pH to 6.4 (5.5 to 6.8) | |

Mix together ingredients. Mix well to form suitable solution. Adjust pH with appropriate buffer. Fill into nebulizer apparatus.

Lung Delivery—Nebulizer Formula (continued)

EXAMPLE 9

| | % |
|---|---|
| Bioactive Agent | 1.0 |
| Water | 57.88 |
| Microcrystalline Cellulose | 1.0 |
| Sodium Carboxymethyl Cellulose | 0.1 |
| benzalkonium chloride | .01 |
| polysorbate 80 | .01 |
| phenyl ethyl alcohol | 40 |
| pH to 6.4 (5.5 to 6.8) | |

Mix together ingredients. Mix well to form suitable solution. Adjust pH with appropriate buffer. Fill into nebulizer apparatus.

Propellant Formula

EXAMPLE 10

| | % |
|---|---|
| Bioactive Agent | 1.0–3.0 |
| ascorbic acid | 0.5 |
| Water | q.s. |
| ethanol | 10 |
| suitable, currently approved propellant (12/11, 12/14 or 12 alone) | 20 |

Mix together all ingredients except propellant. Fill propellant using standard product filling equipment and crimper and pressure filler for the propellant. Such as available from Pamasol Willi Mader, AG.

EXAMPLE 11

| | % |
|---|---|
| Bioactive Agent | 1.0–3.0 |
| ascorbic acid | 0.5 |
| Water | q.s. |
| ethanol | 20 |
| suitable, currently approved propellant (12/11,12/14 or 12 alone) | 30 |

Mix together all ingredients except propellant. Fill propellant using standard product filling equipment and crimper and pressure filler for the propellant. Such as available from Pamasol Willi Mader, AG.

Cited Literature

1. Hougie, C., *Hemophilia and related conditions-congenital deficiencies of prothrombin* (*factor* 11), *factor V and factors VII to XII, in Hematology*. 1983, McGraw-Hill: New York. p. 1381–1399.
2. Mowat, A., The regulation of immune responses to dietary protein antigens. Immuno. Today, 1987.8: p. 93–98.
3. Weiner, H., et al., Oral tolerance: immunologic mechanisms and treatment of animal and human organ-specific autoimmune diseases by oral administration of autoantigens. Annu. Rev. Immunol., 1994.12: p. 809–837.
4. Esmon, C. T., Cell mediated events that control blood coagulation and vascular injury. Annu. Rev. Biol., 1993. 9:1–26: p. 1–26.
5. Stenoflo, J. and Dahlback, *Vitamin K-Dependent Proteins,*
6. Rudnic, E. M., J. A. McCarty, and G. W. Belendiuk, *Hydrophobic Drug Delivery Systems*, 1995, Pharmavene, Inc., Gaithersburg, Md.: USA.
7. Rudnic et al., U.S. Pat. No. 5,430,021.

What is claimed is:

1. A method for treating a patient comprising administering a non-autologous therapeutic antigen to an individual both mucosally and parenterally, said mucosal administration being in an amount effective to reduce an inhibitory immune response to the parenterally administered non-autologous therapeutic antigen.

2. The method of claim 1 wherein the antigen is a polypeptide.

3. The method of claim 2 wherein the polypeptide is a glycoprotein.

4. The method of claim 2 wherein the polypeptide is a cytokine.

5. The method of claim 1 wherein the antigen is a polypeptide which supplements a metabolic deficiency in the recipient of a polypeptide intended to serve the same function.

6. The method of claim 5 wherein the polypeptide which supplements a metabolic deficiency in the recipient is a hormone.

7. The method of claim 6 wherein the hormone is an insulin.

8. The method of claim 2 wherein the polypeptide supplements a deficiency in the recipient in the production of a physiologically important polypeptide.

9. The method of claim 8 wherein the physiologically important polypeptide is a hematologic regulatory factor.

10. The method of claim 9 wherein the hematologic regulatory factor enhances thrombogenesis or platelet deposition.

11. The method of claim 10 wherein the hematologic regulatory factor inhibits thrombogenesis or platelet deposition.

12. The method of claim 1 wherein the antigen is a tissue or cell preparation.

13. The method of claim 12 wherein the tissue or cell preparation contains allogeneic tissue or cells.

14. The method of claim 12 wherein the cell preparation contains xenogeneic tissue or cells.

15. The method of claim 1 wherein the method for reducing an inhibitory immune response to the parenterally administered non-autologous therapeutic antigen comprises mucosally administering the antigen in an amount which induces tolerance to parenteral administration of the non-autologous therapeutic antigen.

16. The method of claim 15 wherein the method for inducing tolerance comprises inducing or elevating a suppressor T cell response to the mucosally administered antigen.

* * * * *